(12) United States Patent
Den Braber

(10) Patent No.: US 9,549,526 B2
(45) Date of Patent: Jan. 24, 2017

(54) RED SPINACH PLANT

(71) Applicant: Rijk Zwaan Zaadteelt en Zaadhandel B.V., De Lier (NL)

(72) Inventor: Jan Hugo Den Braber, Klundert (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 486 days.

(21) Appl. No.: 13/798,335

(22) Filed: Mar. 13, 2013

(65) Prior Publication Data

US 2014/0272083 A1    Sep. 18, 2014

(51) Int. Cl.
*A01H 5/12*    (2006.01)

(52) U.S. Cl.
CPC ..................... *A01H 5/12* (2013.01)

(58) Field of Classification Search
None
See application file for complete search history.

(56) References Cited

U.S. PATENT DOCUMENTS

| 2012/0054894 A1* | 3/2012 | Den Braber | 800/260 |
| 2013/0055424 A1 | 2/2013 | Baerends | |
| 2014/0243931 A1* | 8/2014 | Parker et al. | 607/62 |

FOREIGN PATENT DOCUMENTS

WO    02/42465    5/2002

OTHER PUBLICATIONS

Frieda's Red Heirloom Spinach_2002.*
International Search Report and Written Opinion of the International Searching Authority dated Apr. 17, 2014, which issued during prosecution of International Application No. PCT/EP2014/055012.
Ali, et al. "Comparative study on functional components, antioxidant activity and color parameters of selected colored leafy vegetables as affected by photoperiods" Journal of Food, Agriculture & Environment, Jul. 7, 2009, (3-4):392-398.
Sani, et al. "Potential anticancer effect of red spinach (*Amaranthus gangeticus*) extract" Asia Pacific Journal of Clinical Nutrition, 2004, 13(4):396-400.
Shafaei, et al "Evaluation of 40K in vegetables collected Malaysia by determination total potassium unsing neutron activation analysis" Journal of Radioanalytical and Nuclear Chemistry, Jan. 2011, 288(2):599-602.

* cited by examiner

*Primary Examiner* — David H Kruse
*Assistant Examiner* — Russell Boggs
(74) *Attorney, Agent, or Firm* — Vedder Price P.C.; Thomas J. Kowalski; Deborah L. Lu

(57) ABSTRACT

The present invention relates to a spinach plant (*Spinacia oleracea*) which may comprise a genetic determinant that leads to the plant having a red coloration of the leaves, which genetic determinant may be obtainable from a spinach plant comprising said genetic determinant, representative seed of which was deposited with the NCIMB under accession numbers NCIMB 41954, NCIMB 41955 and NCIMB 41956.

Figure 1:
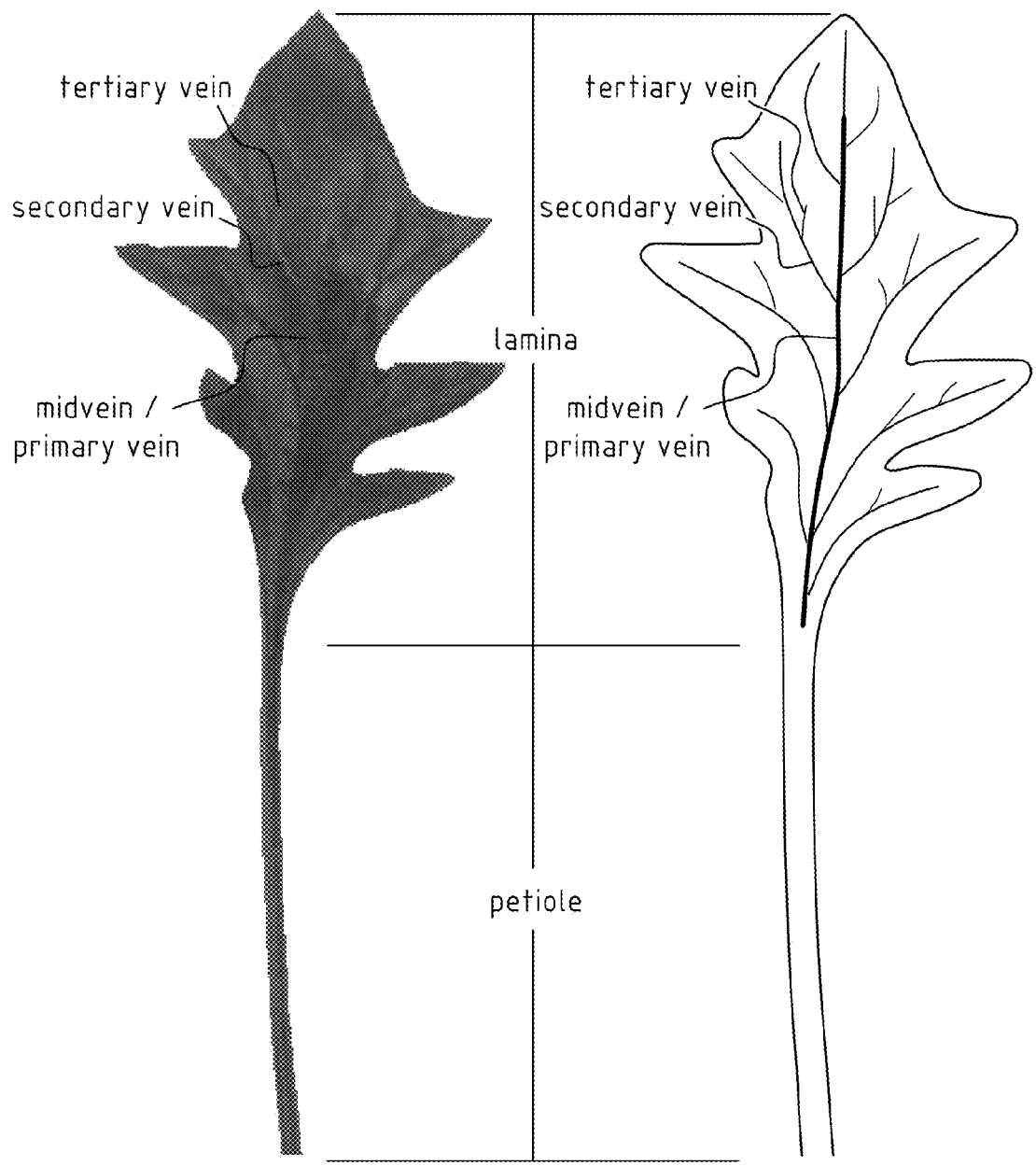

35 Claims, 8 Drawing Sheets
(8 of 8 Drawing Sheet(s) Filed in Color)

RED SPINACH PLANT

INCORPORATION BY REFERENCE

All documents cited or referenced herein ("herein cited documents"), and all documents cited or referenced in herein cited documents, together with any manufacturer's instructions, descriptions, product specifications, and product sheets for any products 5 mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a red spinach plant (*Spinacia oleracea* L.). The invention also relates to the seeds and progeny of such plants and to propagation material for obtaining such plants. This invention further relates to the use of plants, seeds and propagation material derived from such plants as germplasm in a breeding programme.

BACKGROUND OF THE INVENTION

Spinach (*Spinacia oleracea* L.) is a flowering plant of the Amaranthaceae family that is grown as a vegetable. The edible parts of the spinach plant are the leaves of the vegetative stage. During the vegetative stage spinach produces a rosette of leaves. These leaves are crinkly and curly in the case of savoy leaf types, slightly crinkled in the case of semi-savoy leaf types, or broad and flat in the case of smooth leaf types. The leaves of a spinach plant are usually sold fresh clipped and bagged, fresh bunched, canned or frozen. The dominant spinach product in the market is the fresh clipped and bagged spinach. This bagged product is sold as either baby spinach containing very small, young leaves, or as teenage spinach containing slightly older, medium-sized leaves. Both baby and teenage spinach leaf sizes are smaller than the leaf sizes at harvest of bunched, frozen or canned spinach. Usually the harvested leaves of baby spinach are no longer than about eight centimeter. These tender, sweet leaves are often used in salads, but can also be lightly cooked or steamed.

Lifestyles change and the demand from restaurants, catering firms and even from the customer in the supermarket for colourful and attractive leafy vegetables for salads or other dishes continues to rise. As a result, vegetable breeding companies are looking for varieties with prominent colour, better taste and a wide variety of textures.

Though spinach (*Spinacia oleracea* L.) is a popular product due to its attractive taste and high nutritional value, at present spinach cannot add a lot of colour other than green to dishes or salad mixes. The most colourful spinach (*Spinacia oleracea* L.) that has been known so far has green leaves with a red petiole and red major veins. These plants have green leaves with a red colouration of the leaves that is confined to the petiole and leaf blade areas where the primary, secondary, and in some cases also tertiary, veins are located, while the leaf blade areas between the veins are green. An example of such a plant is presented in FIG. 2D.

FIG. 1 shows a picture and a schematic representation of a spinach leaf, indicating the petiole and the lamina, which is often indicated as the leaf blade, with its primary, secondary and tertiary veins.

Citation or identification of any document in this application is not an admission that such document is available as prior art to the present invention.

SUMMARY OF THE INVENTION

Given the need for spinach (*Spinacia oleracea* L.) with leaves with more red colouration, it is the object of the present invention to provide a spinach (*Spinacia oleracea* L.) plant that has more of the colour red than the spinach plants known so far.

In the research leading to the present invention a new spinach plant (*Spinacia oleracea* L.) was created which may comprise a genetic determinant that leads to the plant having a red colouration of the leaves, wherein at least part of the cells of the epidermis of the spinach leaf between the veins of at least the adaxial (upper) leaf surface, preferably both the adaxial and abaxial (lower) leaf surface, comprise a red pigment.

The spinach plants of the invention are both attractive and tasty. In addition, they are more healthy than plants not carrying the genetic trait of the invention. The betacyanin level is increased in plants of the invention and betacyanins have been reported to have several health benefits. Betacyanins exhibit excellent antioxidant activity. Moreover, anti-cancer effects have been reported for betacyanins.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seeds of *Spinacia oleracea* L. 12.3002, 12.3007 and 12.3009 that comprise the genetic determinant of the invention which leads to the plant having a red colouration of the leaves, wherein at least part of the cells of the epidermis of the spinach leaf between the veins of the adaxial and/or abaxial leaf surface comprise a red pigment, were deposited with NCIMB Ltd, Ferguson Building, Craibstone Estate, Bucksburn, Aberdeen AB21 9YA, UK, on 6 Apr. 2012 under deposit accession numbers NCIMB 41954, NCIMB 41955 and NCIMB 41956. Seeds of these deposits comprise the genetic determinant in a homozygous state. The deposited seeds do not meet the DUS criteria which are required for obtaining plant variety protection, and can therefore not be considered to be plant varieties.

The Deposits with NCIMB, under deposit accession number NCIMB 41859 were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the 15 patent, whichever is longer, and will be replaced if necessary during that period.

FIGURES

The patent or application file contains at least one drawing executed in color. Copies of this patent or patent application publication with color drawing(s) will be provided by the Office upon request and payment of the necessary fee.

In the examples reference is made to the following figures:

FIG. 1: Picture and schematic representation of a spinach leaf. The petiole, lamina (also called leaf base) and primary (also called midvein), secondary and tertiary veins of the leaf are indicated.

Figure 2A:
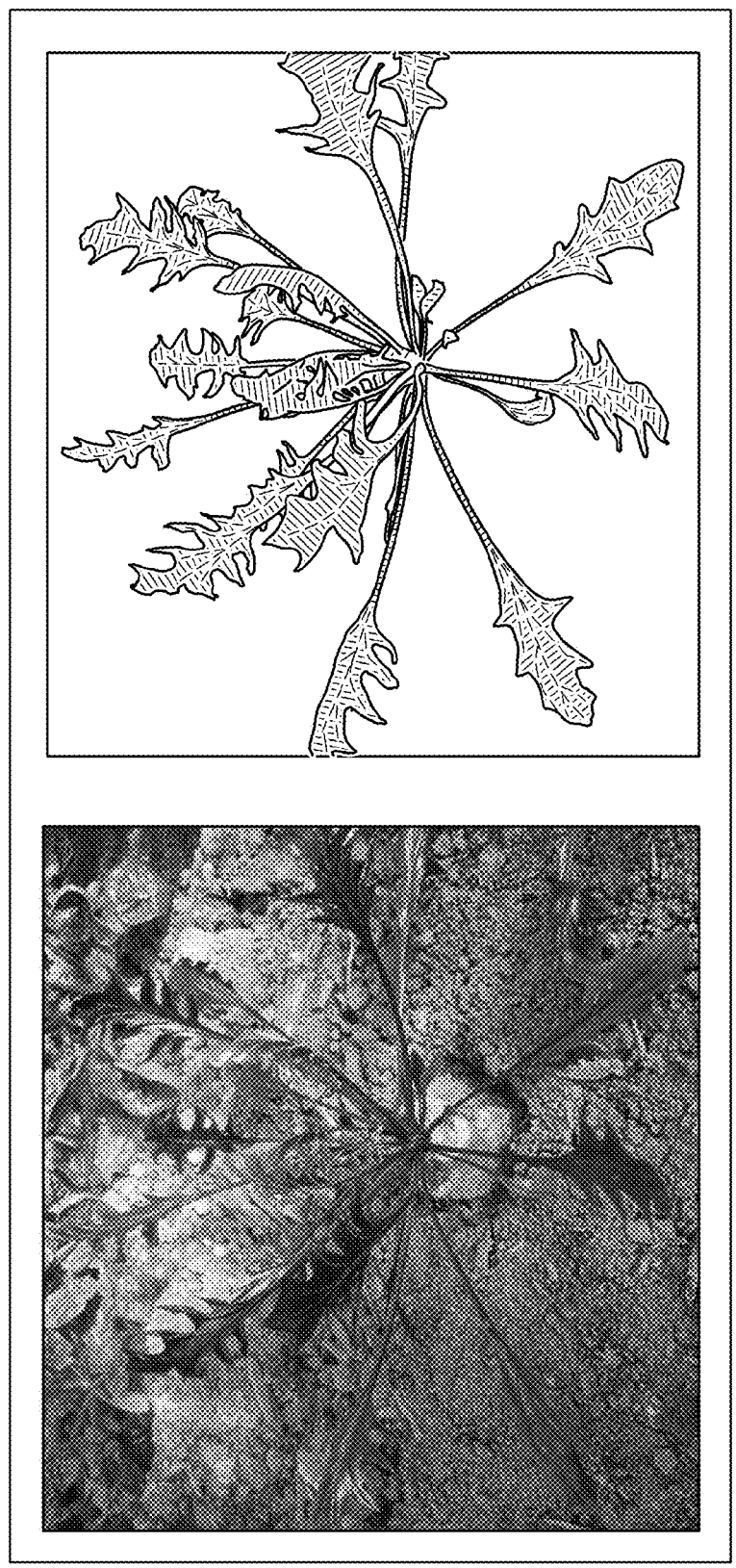

FIG. 2A: Picture and schematic representation of a spinach plant of the invention carrying the genetic determinant homozygously. In the schematic representation of a plant of the invention the shading indicates areas of the plant that have a red colour; the dashed lines indicate the veins that have a red colour. The lines that are not dashed indicate veins that are not coloured red.

Figure 2B:
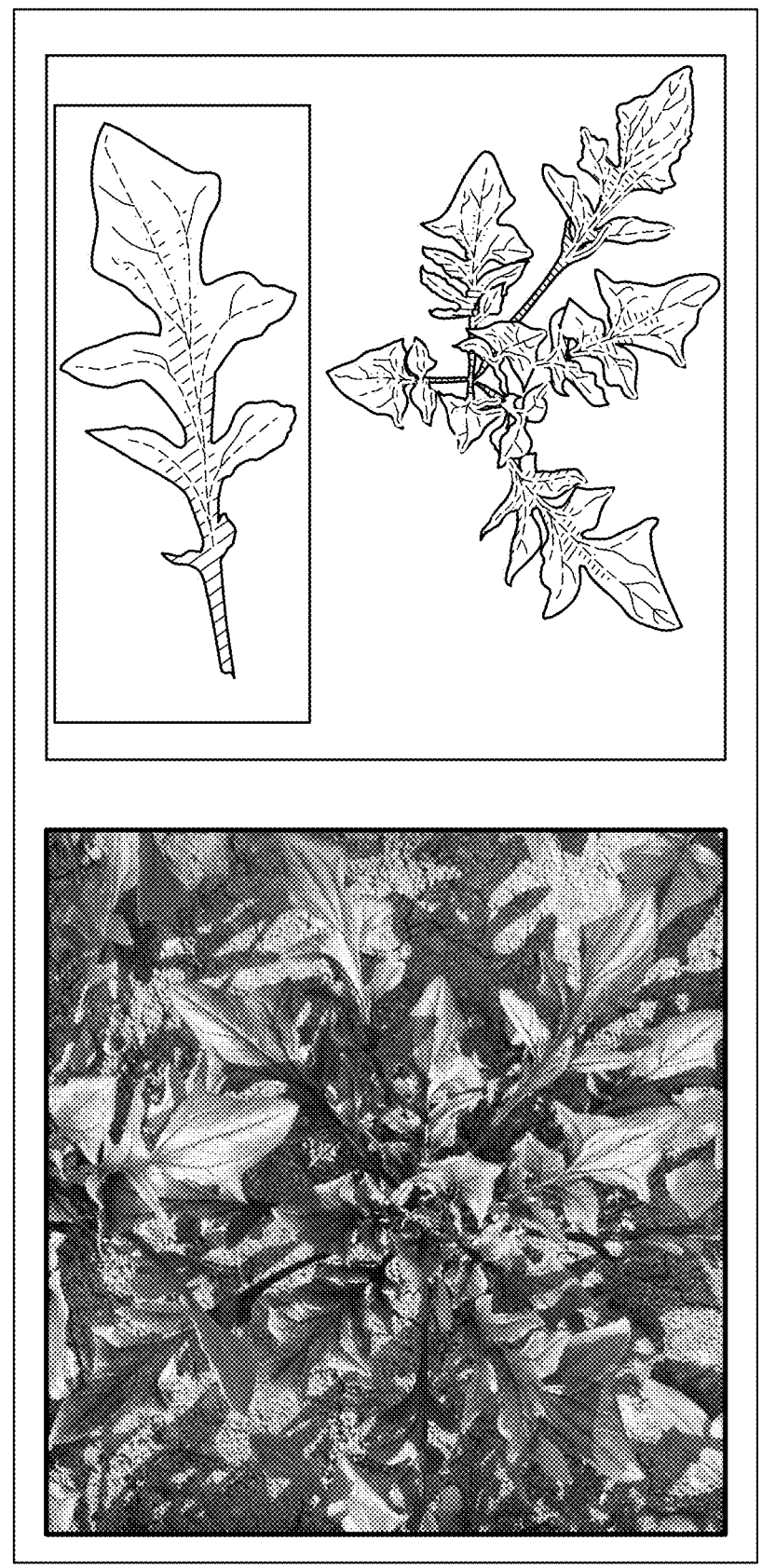

FIG. 2B: Picture and schematic representation of a spinach plant of the invention carrying the genetic determinant heterozygously. In the schematic representation both an example of a complete plant is drawn and one example of a leaf of such a plant. The shading indicates areas of the plant that have a red colour; the dashed lines indicate the veins that have a red colour. The lines that are not dashed indicate veins that are not coloured red.

Figure 2C:
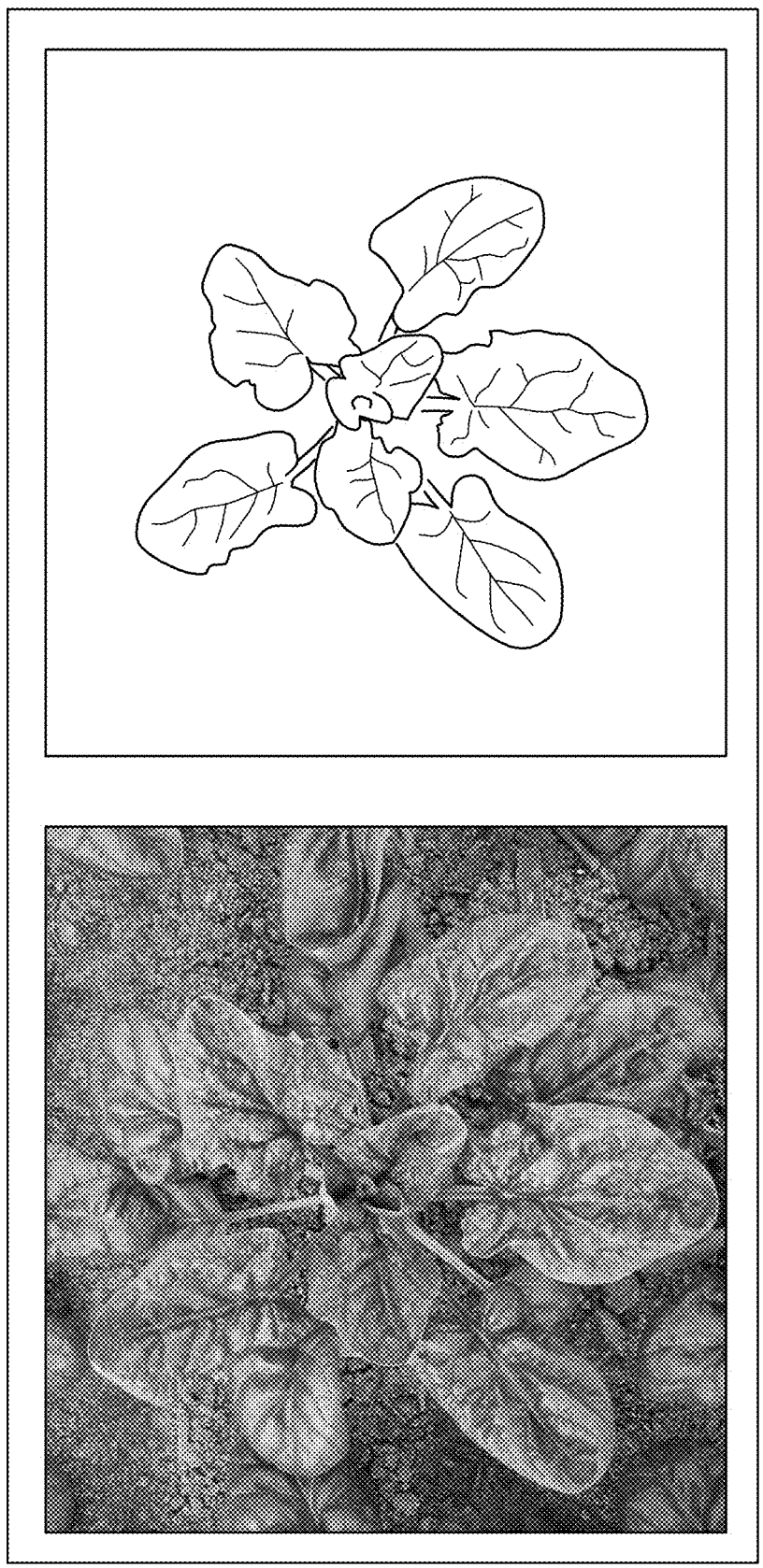

FIG. 2C: Picture and schematic representation of a plant of a green spinach variety (Squirrel). The shading indicates areas of the plant that have a red colour; the dashed lines indicate the veins that have a red colour. The lines that are not dashed indicate veins that are not coloured red.

Figure 2D:
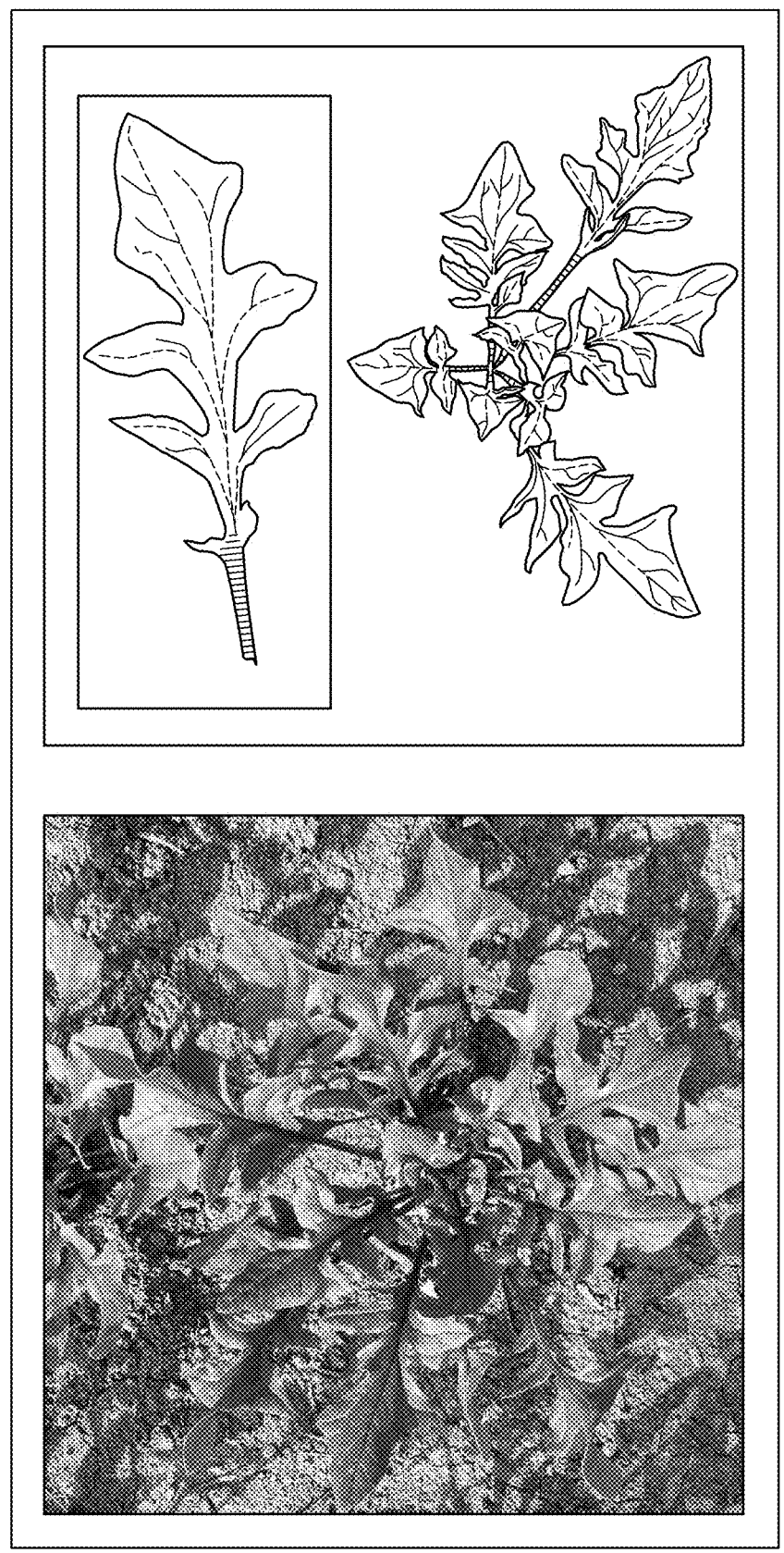

FIG. 2D: Picture and schematic representation of a spinach plant with green leaves with red petioles and red major veins (red veined spinach). In the schematic representation both an example of a complete plant is drawn and one example of a leaf of such a plant. The shading indicates areas of the plant that have a red colour; the dashed lines indicate the veins that have a red colour. The lines that are not dashed indicate veins that are not coloured red.

Figure 3A:
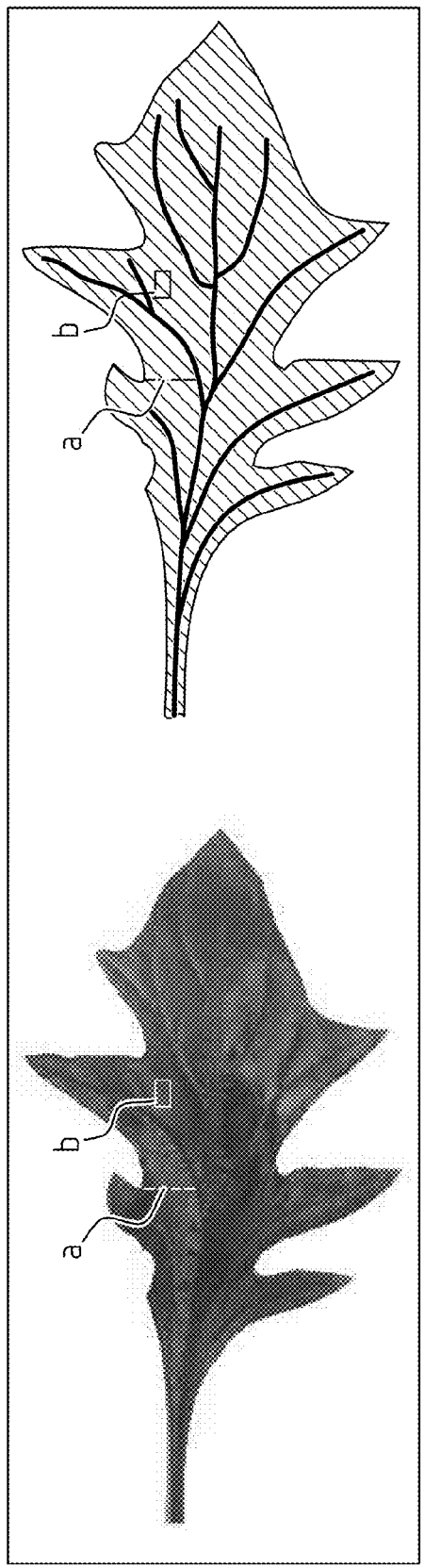

FIG. 3A: Picture and schematic representation of the adaxial (upper) side of a spinach leaf of the invention. The rectangle (b) indicates an example of an area of the leaf in between the veins for taking epidermal strips such as the ones pictures in FIG. 3C-F. The dotted line (a) indicates an example of where a transverse section of the leaf such as the ones presented in FIGS. 3G and 3H, not including any major veins, may be taken.

Figure 3B:
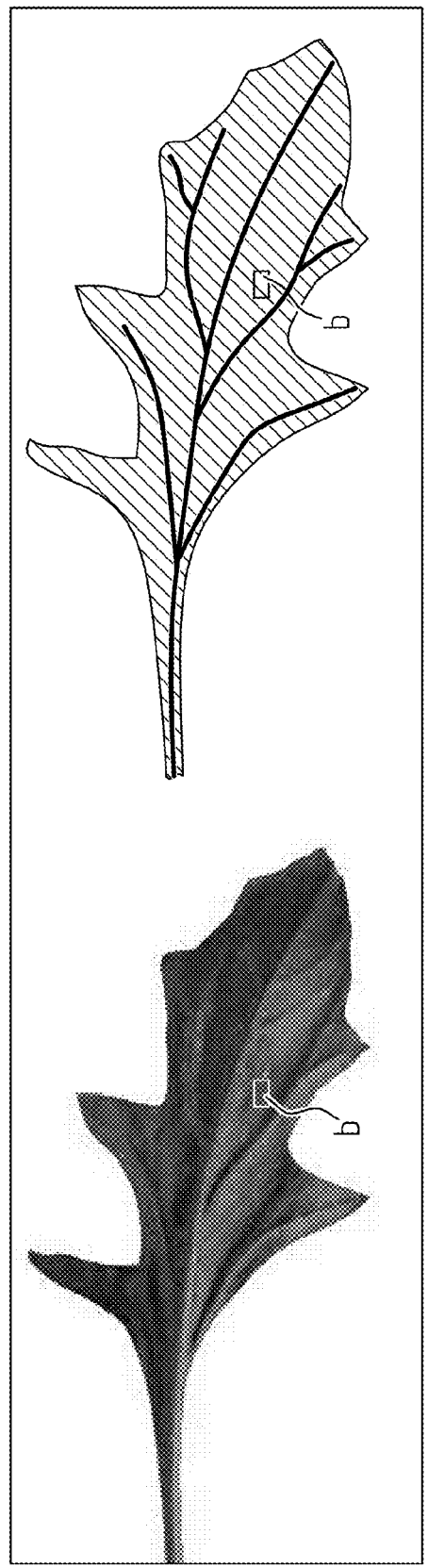

FIG. 3B: Picture and schematic representation of the abaxial (lower) side of a spinach leaf of the invention. The rectangle (b) indicates an example of an area of the leaf in between the veins for taking epidermal strips such as the ones pictures in FIG. 3C-F.

Figure 3C:
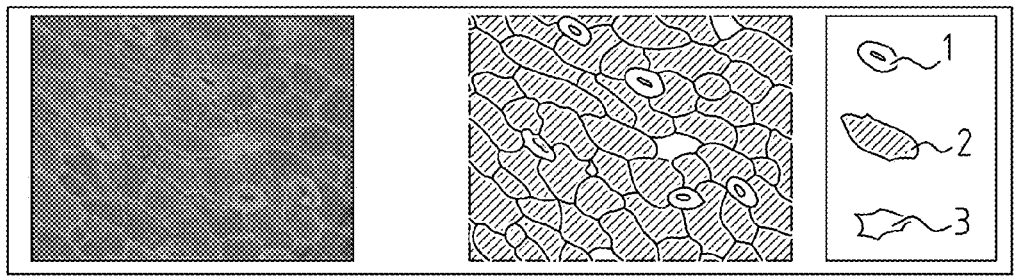

FIG. 3C: Epidermis of an area in between the veins of a leaf of a plant of the invention carrying the genetic determinant homozygously. The shading indicates cells that have a red colour and thus comprise red pigment. An example of such a cell is indicated by (2). An example of an epidermis cell not comprising red pigment is indicated by (3). In the epidermis stomata (1) are found, the cells of the stomata (also called guard cells) do not have a red colour.

Figure 3D:
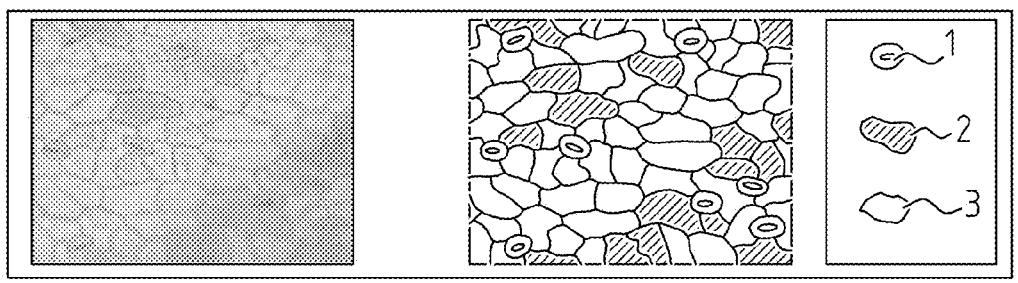

FIG. 3D: Epidermis of an area in between the veins of a leaf of a plant of the invention carrying the genetic determinant heterozygously. The shading indicates cells that have a red colour and thus comprise red pigment. An example of such a cell is indicated by (2). An example of an epidermis cell not comprising red pigment is indicated by (3). In the epidermis stomata (1) are found, the cells of the stomata (also called guard cells) do not have a red colour.

Figure 3E:
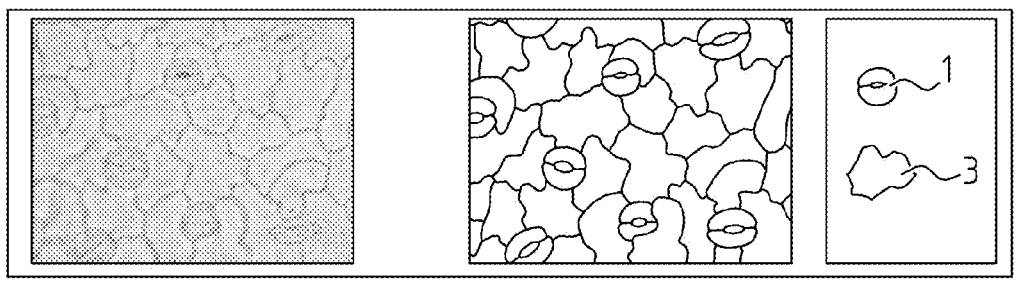

FIG. 3E: Epidermis of an area in between the veins of a leaf of green spinach plant. The shading indicates cells that have a red colour and thus comprise red pigment. In this case no cells in the epidermal strip have a red colour. An example of an epidermis cell not comprising red pigment is indicated by (3). In the epidermis stomata (1) are found, the cells of the stomata (also called guard cells) do not have a red colour.

Figure 3F:
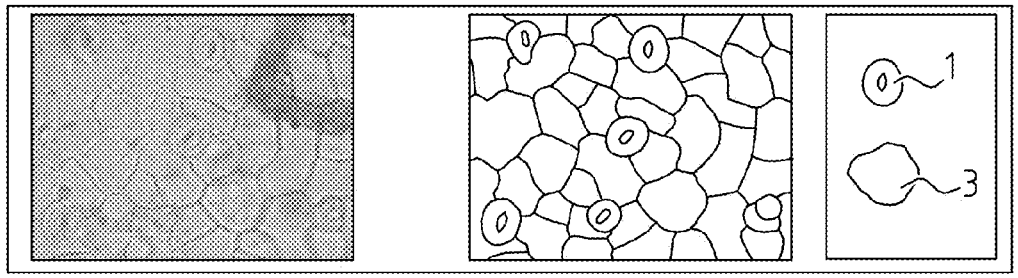

FIG. 3F: Epidermis of an area in between the veins of a leaf of a plant with green leaves with red petioles and red major veins (red veined spinach). The shading indicates cells that have a red colour and thus comprise red pigment. In this case no cells in the epidermal strip have a red colour. An example of an epidermis cell not comprising red pigment is indicated by (3). In the epidermis stomata (1) are found, the cells of the stomata (also called guard cells) do not have a red colour.

Figure 3G:
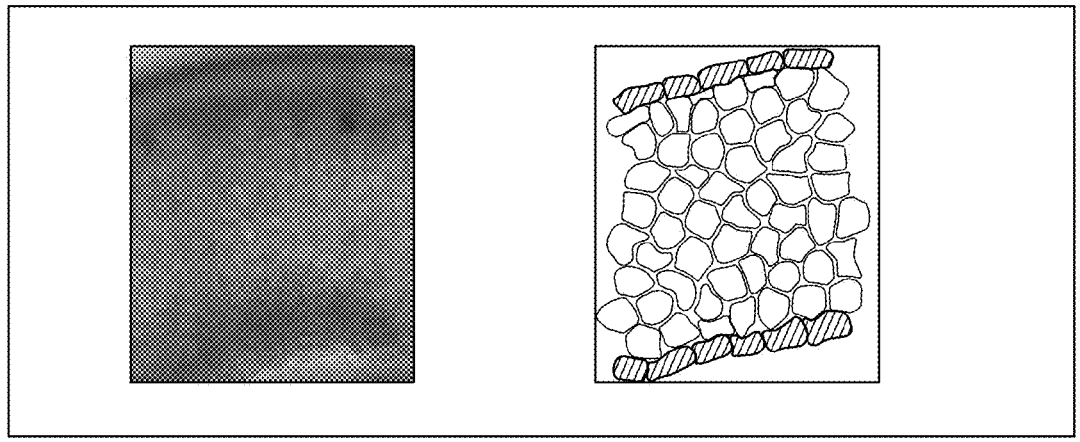

FIG. 3G: Picture and schematic representation of a transverse section of a leaf of a plant of the invention. The shading in the schematic representation indicates cells that have a red colour and thus comprise red pigment.

Figure 3H:
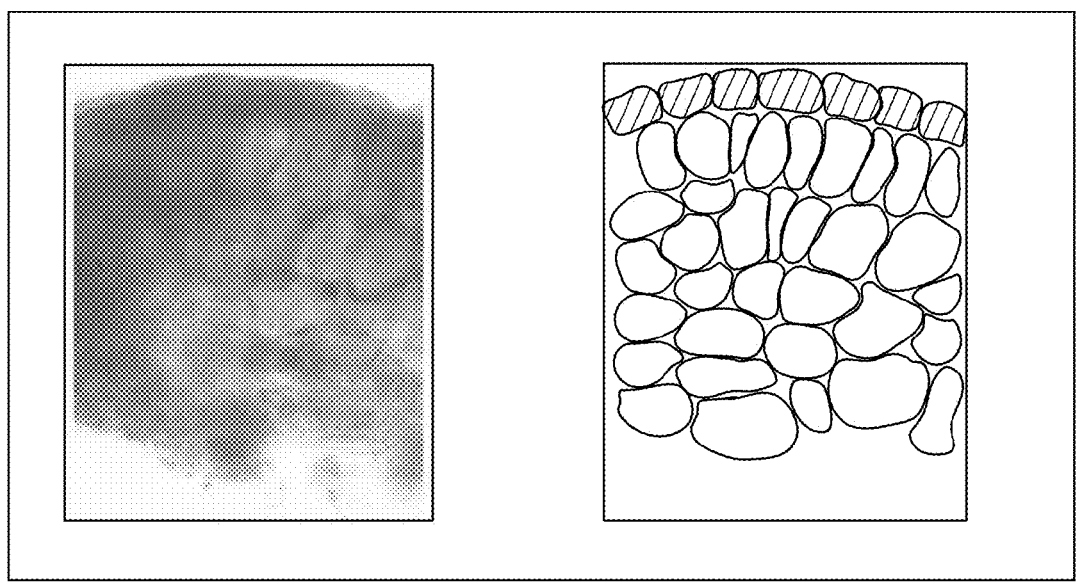

FIG. 3H: Picture and schematic representation of a transverse section of a leaf of a plant of the invention. In this transverse section only one epidermal cell layer and several layers of mesophyll cells are visible. The shading in the schematic representation indicates cells that have a red colour and thus comprise red pigment.

DETAILED DESCRIPTION OF THE INVENTION

The present invention thus provides a spinach plant (*Spinacia oleracea* L.) which may comprise a genetic determinant that leads to the plant having a red colouration of the leaves, wherein at least part of the cells of the epidermis of the spinach leaf between the veins of at least the adaxial leaf surface, preferably both the adaxial and abaxial leaf surface, comprise a red pigment, which genetic determinant is as comprised in a spinach plant representative seed of which was deposited with the NCIMB under accession numbers NCIMB 41954, NCIMB 41955 and NCIMB 41956.

In this context "spinach" is intended to comprise *Spinacia oleracea* L.

The trait of the present invention is determined by a semi-dominant or incomplete dominant genetic determinant. In cases of incomplete dominance or semi-dominance, the phenotype of the heterozygote is intermediate between those of the parent homozygotes. This type of inheritance may also be indicated as intermediate inheritance. The genetic determinant may be present in homozygous or heterozygous state to result in the phenotypic trait of the invention.

The genetic determinant of the invention behaves as a single semi-dominant or incomplete dominant locus. This locus may be a gene or an allele and may also include regulatory elements.

In this context the "genetic determinant" is the underlying genetic element that causes the phenotypic trait of the invention. The "phenotypic trait" is the phenotype in which the plant has a red colouration of the leaves, wherein at least part of the cells of the epidermis of the spinach leaf between the veins of at least the adaxial leaf surface, preferable both the adaxial and abaxial leaf surface, comprise a red pigment. "Genetic trait", "trait" and "phenotypic trait" may be used interchangeably.

A representative sample of spinach (*Spinacia oleracea* L.) seed which may comprise the genetic determinant which when present leads to the plants having a red colouration of the leaves, wherein at least part of the cells of the epidermis of the spinach leaf between the veins of at least the adaxial leaf surface, preferably both the adaxial and abaxial leaf surface, comprise a red pigment, has been deposited on 6 Apr. 2012 at the NCIMB in Aberdeen under accession numbers NCIMB 41954, NCIMB 41955 and NCIMB 41956. Seeds of these deposits comprise the genetic determinant homozygously. The deposits do not fulfil the requirements of uniformity and stability and therefore they do not constitute plant varieties.

The genetic determinant that confers the phenotypic trait of the invention is transferable to all *Spinacia oleracea* L. types, such as savoy, semi-savoy and smooth spinach types.

The red colouration of the complete or partial leaves of plants of the invention is a purple-red, or burgundy red-like colour. The red colour of the complete or partial leaves of plants of the invention is easily observable by the skilled person but may also be determined using the RHS colour chart (The Royal Horticultural Society, London, UK). On this chart the red colouration of the invention resembles the colours 187A, 187B, 187C, 187D, N186B, N186C or N186D.

In one embodiment the present invention relates to a spinach (*Spinacia oleracea* L.) plant which may comprise the genetic determinant of the invention, wherein the genetic determinant is present in a heterozygous state.

Plants of the invention carrying the genetic determinant heterozygously may be identified by the red colouration of the leaves of the invention as depicted in FIG. 2B, optionally already at the moment the first two leaves of the plants are at harvestable stage, preferably at the moment the first two leaves of the plant are fully grown.

The term "harvestable stage" is clear to the skilled spinach grower and means in particular the leaf stage from baby leaf stage, through to mature leaf stage, before the spinach plant starts bolting and an inflorescence stem develops. "Harvestable stage", "harvesting stage" and "harvest stage" may be used interchangeably.

The skilled spinach grower knows when the baby leaf stage is reached and the spinach is harvestable. The younger the plants are at harvest, the smaller and more tender their leaves are, which is appreciated by the customer. On the other hand, if spinach is harvested very early the grower will get less kilograms of product from his field. The skilled spinach grower will balance these two things out to make maximum profit. Baby leaf spinach is typically grown at a density of 8 million seeds/ha and harvested when the spinach plants are about 10 cm high, though baby leaf spinach may be harvested even earlier and/or grown at a different density. At baby leaf stage the spinach plant typically has at least two fully grown leaves. With leaves the true leaves are meant that start developing after the cotyledons have been formed.

In plants of the invention carrying the genetic determinant heterozygously the leaves are at least partially red at harvesting stage. In particular said plants have red petioles and leaf blades with red primary and secondary veins and additional reddish colouration in the leaf areas of the adaxial surface (i.e. the upper side) of the leaf in between these veins. An example of such a plant is presented in FIG. 2B. In said plants of the invention the red colouration is, thus, not limited to the petioles and the leaf area at the major veins.

The percentage of the leaf showing a reddish colouration in plants carrying the genetic determinant of the invention heterozygously differs from one genetic background to another, but is always higher than in red vein spinach plants not carrying the genetic determinant of the invention, when grown under identical circumstances.

In some plants carrying the genetic determinant of the invention heterozygously the red colouration may be more confined to the areas close to the major veins of the leaf, whereas in other plants carrying the genetic determinant of the invention heterozygously the red pigment may be present in leaf epidermal cells almost throughout the leaf blade.

Plants of the invention may be analysed by examining whether the cells of the epidermis of the spinach leaf between the veins of the adaxial and abaxial leaf surface are red. This may be done by peeling off the epidermal cell layer from either the adaxial or abaxial surface of the leaf with a sharp forceps and subsequent transmitted light microscopy.

In plants of the invention carrying the genetic determinant heterozygously about, in order of increased preference, 10-100%, 15-90%, 20-80%, 30-70% of the cells of the epidermis of the spinach leaf between the veins of at least the adaxial leaf surface, preferably both the adaxial and abaxial leaf surface, excluding the cells of the stomatal complex, comprise a red pigment.

In a further embodiment the invention relates to a spinach (*Spinacia oleracea* L.) plant which may comprise the genetic determinant of the invention in a homozygous state.

Plants of the invention carrying the genetic determinant homozygously may be identified by their red petioles and the red colouration of their leaves, optionally already at the moment the first two leaves of the plants are at harvestable stage, preferably at the moment the first two leaves of the plant are fully grown.

An example of a plant of the invention carrying the genetic determinant homozygously is presented in FIG. 2A.

Plants of the invention carrying the genetic determinant homozygously have a red colouration of the aboveground vegetative parts of the plant.

The term "aboveground vegetative plant parts" as used herein is intended to mean the aboveground parts of the plant that are not involved in sexual reproduction, excluding the hypocotyl and cotyledons, including the leaves, stem and petioles.

It was found that inflorescences and flowers of plants of the invention carrying the genetic determinant homozygously may also have a red colouration.

Plants of the invention carrying the genetic determinant homozygously, have a red colouration over the entire surface of the leaves of the plant at harvesting stage. Said plants in particular have a uniform red colouration over the entire surface of the leaves of the plant at harvesting stage.

The red colour of the aboveground vegetative parts, and in particular the leaves at harvesting stage, of plants of the invention carrying the genetic determinant homozygously is a purple-red, or burgundy red-like colour.

Red as used in this application includes the colour that is perceived as purple.

The red colour of the aboveground vegetative parts of plants of the invention may be determined using the RHS colour chart (The Royal Horticultural Society, London, UK) and is preferably selected from colours with RHS codes 187A, 187B, 187C, 187D, N186B, N186C and/or N186D, or combinations thereof. This red colour is in particular visible in plants grown from seeds deposited with the NCIMB under accession numbers NCIMB 41954, NCIMB 41955 and NCIMB 41956. In different spinach types or varieties the colour may differ, but will still be perceived as red by the skilled person.

Though the RHS colour chart is commonly used by plant breeders and growers for determining plant colours, it is clear the colour may also be determined using other colour charts or systems. Colours may, for example, also be specified in RGB colour codes, using the Munsell colour system or may be determined using a colorimeter. The skilled person knows how to use these different colour systems and convert colour codes between different colour systems. The RGB, CIELab and CIELCh values for these RHS colours are listed in the table below.

| | sRGB | | | CIE Lab D65/10° | | | CIE LCh D65/10° | | |
|---|---|---|---|---|---|---|---|---|---|
| RHS | R | G | B | L | a | b | L | C | h |
| N186B | 74 | 63 | 77 | 28 | 8 | -8 | 28 | 11 | 318 |
| N186C | 96 | 62 | 70 | 30 | 16 | 1 | 30 | 16 | 3 |
| N186D | 131 | 53 | 79 | 34 | 37 | 1 | 34 | 37 | 1 |
| 187A | 92 | 53 | 62 | 27 | 19 | 2 | 27 | 19 | 5 |
| 187B | 113 | 51 | 66 | 30 | 29 | 4 | 30 | 29 | 7 |
| 187C | 129 | 55 | 72 | 34 | 34 | 5 | 34 | 34 | 8 |
| 187D | 148 | 54 | 85 | 37 | 43 | 2 | 37 | 42 | 3 |

In particular at least the adaxial surface, preferably both the adaxial and abaxial surface, of the harvestable leaves of plants of the invention carrying the genetic determinant homozygously have the colour as defined above.

The red pigment of the harvestable leaves of plants of the invention carrying the genetic determinant homozygously is primarily localised in the epidermis of the leaf (as depicted in FIG. 3H) of, at least the adaxial surface, preferably both the adaxial and abaxial surface (as depicted in FIG. 3G), of the leaf.

Within the epidermis of the leaf the red pigment is comprised within the epidermal cells, excluding the guard cells of the stomatal complex. Said red pigment may be present in additional cells besides those of the epidermis.

In plants of the invention carrying the genetic determinant homozygously about, in order of increased preference, 50-100%, 60-100%, 70-100%, 80-100%, 90-100%, 95-100% of the cells of the epidermis of the spinach leaf between the veins of at least the adaxial surface, preferably both the adaxial and abaxial surface, excluding the cells of the stomatal complex, comprise a red pigment.

In one embodiment the invention relates to a spinach (*Spinacia oleracea* L.) plant which may comprise the genetic determinant of the invention, wherein the betacyanin content of the leaves at harvest stage is at least, in order of increased preference, 90 μg betanin equivalents/g fresh weight, 100 μg betanin equivalents/g fresh weight, 110 μg betanin equivalents/g fresh weight, 120 μg betanin equivalents/g fresh weight, 130 μg betanin equivalents/g fresh weight, 140 μg betanin equivalents/g fresh weight, 150 μg betanin equivalents/g fresh weight, 160 μg betanin equivalents/g fresh weight, 170 μg betanin equivalents/g fresh weight, 180 μg betanin equivalents/g fresh weight, 190 μg betanin equivalents/g fresh weight, 200 μg betanin equivalents/g fresh weight, 210 μg betanin equivalents/g fresh weight, 220 μg betanin equivalents/g fresh weight, 230 μg betanin equivalents/g fresh weight, 240 μg betanin equivalents/g fresh weight, 250 μg betanin equivalents/g fresh weight, 300 μg betanin equivalents/g fresh weight, 350 μg betanin equivalents/g fresh weight, 400 μg betanin equivalents/g fresh weight, 450 μg betanin equivalents/g fresh weight, 500 μg betanin equivalents/g fresh weight, 550 μg betanin equivalents/g fresh weight, 600 μg betanin equivalents/g fresh weight. The betacyanin content of the leaves at harvesting stage is suitably not higher than 1000 μg betanin equivalents/g fresh weight.

Betacyanins are the red-purple pigments falling within the group of the betalains. Betalains are nitrogen-containing water-soluble compounds derived from tyrosine that are found in only a limited number of plant lineages (Tanaka et al., The Plant Journal (2008) 54, 733-749). Betalains show brilliant colours in flowers, fruits and other plant parts of species belonging to the families of Caryophyllales, except for Caryophyllaceae and Molluginaceae. Betalains from red beet (*Beta vulgaris*) are used as a natural colorant. The advantage of betalain colour is that the colour does not depend on the pH and is more stable than that from anthocyanins. Betalains are classified into red (crimson, purple, violet) betacyanins and yellow betaxanthins. They are immonium conjugates of betalamic acid with cyclo-dihydroxyphenylalanine (cDOPA) glucoside and amino acids or amines, respectively. Only betacyanins are modified by glycosyl or acyl moieties. More than 50 molecular species of betacyanins and several betaxanthins have been isolated and identified. Betalains accumulate in vacuoles in epidermal and subepidermal tissue layers, in both vegetative and reproductive tissues.

Examples of betacyanins are betanin, isobetanin, probetanin, neobetanin, amaranthine, isoamaranthine, iresins (acylated amaranthine), celosianins (acylated amaranthine), gomphrenin I, isogomphrenin I, acelated gomphrenins. The relative level and absence or presence of each of these pigments in plants producing betacyanins varies between species.

Betacyanin content in any plant tissue may be measured by making a sample solution in an extraction buffer, measuring the absorbance spectrum using a spectrophotometer and quantifying the betacyanin absorbance peak. Alternatively, total betacyanin content may be measured using HPLC (high-performance liquid chromatography), possibly combined with mass spectrometry methods like for example MALDI-TOF (matrix-assisted laser desorption/ionization) or Q-TOF (tandem mass spectrometry). Using HPLC or mass spectrometry methods like MALDI-TOF or Q-TOF it is possible to identify the levels of different betacyanins (like for example betanin, amaranthine, gomphrenin). The total betacyanin content may then be calculated by adding up the levels of the different betacyanin pigments identified. The skilled person knows how to perform such analyses and make such calculations.

The betacyanin content of the leaves of spinach plants at harvest stage may be measured by taking a representative sample of, for example, about 200 grams of fresh weight of the above ground portion harvested at the mature leaf stage and sampling, for example, two samples of 5-10 plants to serve as replicates.

In case a Potassium phosphate buffer (250 mM, pH=5) is used as an extraction liquid and the absorbance spectrum is measured using a spectrophotometer, at least the absorbance at 537 nm has to be determined to determine the betacyanin content of the sample. The skilled person may then calculate the amount of total betacyanin using a formula which uses the extinction coefficient of, for example, betanin in said Potassium phosphate buffer used. In that case the total betacyanin level may be given in μg betanin equivalents/g fresh weight (FW).

The values for the betacyanin content as listed herein have been obtained using a potassium phosphate buffer (250 mM, pH=5) as an extraction liquid, measuring the absorbance of the sample at 537 nm using a spectrophotometer and calculating the amount of total betacyanin using a formula which uses the extinction coefficient of betanin in said Potassium phosphate buffer.

The present invention also relates to a spinach (*Spinacia oleracea* L.) plant which may comprise the genetic determinant of the invention, wherein the ratio between total chlorophyll and total betacyanin as calculated in betanin equivalents (μg total chlorophyll/g fresh weight μg divided by μg betanin equivalents/g fresh weight) of the leaves at harvest stage lies, in order of increased preference, between 0.001 and 29, between 0.01 and 25, between 0.10 and 15, between 0.25 and 10, between 0.5 and 5.

The total chlorophyll content of the leaves of spinach plants at harvest stage may be measured by taking a representative sample of, for example, about 200 grams of fresh weight of the above ground portion harvested at harvest stage, preferably at roughly identical stage for the spinach plants to be compared, and taking, for example, two samples of 5-10 plants each to serve as replicates. Total chlorophyll content may, for example, be determined by measuring the absorbance spectrum of the sample solution in extraction liquid using a spectrophotometer, quantifying the chlorophyll A and chlorophyll B absorbance peak and calculating the total chlorophyll level. The skilled person is familiar with these methods.

This invention also relates to spinach plants of the invention, obtainable by crossing a first spinach plant with a second spinach plant, wherein at least one of the said plants may comprise the genetic determinant as comprised in a spinach plant representative seed of which was deposited with the NCIMB under accession numbers NCIMB 41954, NCIMB 41955 and NCIMB 41956, or a progeny plant thereof carrying the genetic determinant, and selecting, preferably in the F2 generation, for plants having a red colouration of the leaves, wherein at least part of the cells of the epidermis of the spinach leaf between the veins of at least the adaxial leaf surface, preferably both the adaxial and abaxial leaf surface, comprise a red pigment.

The trait of the invention may be brought into a wild type spinach plant by crossing the wild type plant with a plant that is either homozygous or heterozygous for the genetic determinant of the invention and selecting for the desired phenotype in the progeny of that cross, preferably in the F1 and F2 of that cross, by selecting for plants having a red colouration of the leaves, wherein at least part of the cells of the epidermis of the spinach leaf between the veins of at least the adaxial leaf surface, preferably both the adaxial and abaxial leaf surface, comprise a red pigment.

When using a plant of the invention carrying the genetic determinant heterozygously in a cross with a wild type plant such selection in the F1 of that cross is necessary, as in that case only about 50% of the F1 plants will carry the genetic determinant of the invention.

When using a plant of the invention carrying the genetic determinant homozygously in a cross with a wild type plant, on the other hand, normally all F1 plants from that cross will have carry the genetic determinant of the invention heterozygously and may be used for selfing to produce F2 populations that also contain plants carrying the genetic determinant of the invention homozygously.

Spinach plants carrying the genetic determinant of the invention leading to the trait of having a red colouration of the leaves, wherein at least part of the cells of the epidermis of the spinach leaf between the veins of at least the adaxial leaf surface, preferably both the adaxial and abaxial leaf surface, comprise a red pigment, may suitably be identified among descendants from a cross between a plant not comprising the genetic determinant, and a plant which may comprise the genetic determinant in a homozygous state, by growing F2 plants from, for example, about 12 seeds that are the result from the initial cross and a selfing step, and selecting plants showing the desired trait of the invention.

Alternatively, spinach plants carrying the genetic determinant of the invention leading to the trait having a red colouration of the leaves, wherein at least part of the cells of the epidermis of the spinach leaf between the veins of at least the adaxial leaf surface, preferably both the adaxial and abaxial leaf surface, comprise a red pigment, may suitably be identified among descendants from a cross between a plant not comprising the genetic determinant, and a plant which may comprise the genetic determinant in a heterozygous state, by selecting F1 plants resulting from the initial cross that show the phenotypic trait of plants which may comprise the genetic determinant of the invention heterozygously, self pollinating those plants and growing F2 plants out of, for example, about 12 seeds they produce, and selecting plants showing the desired trait.

Selecting the plants may be done phenotypically as both the plants carrying the genetic determinant in a homozygous state and those carrying the genetic determinant in a heterozygous state may be easily identified by the red colouration of their leaves. The red colouration of the spinach plants of the invention thus serves as a visual marker. Alternatively, selection may be done through identification of the genetic determinant, for example by means of one or more molecular markers. Markers may be developed accordingly by a skilled person based on the material that was deposited under number NCIMB 41954, NCIMB 41955 and NCIMB 41956.

When more than one gene may be responsible for a certain trait, an allelism test may be done to determine equivalence. The skilled person doing the test has to make sure that all relevant genes are present homozygously for the test to work properly.

Equivalence of genetic determinants may thus be determined by an allelism test. To perform an allelism test, material that is homozygous for the known determinant, a tester plant, is crossed with material that is homozygous for the genetic determinant that is to be tested. This latter plant is referred to as the donor plant. The donor plant to be tested should be or should be made homozygous for the genetic determinant to be tested. The skilled person knows how to obtain a plant that is homozygous for the genetic determinant to be tested. When in the F2 of the cross between a donor plant and a tester plant no segregation for the phenotype related to the genetic determinant is observed, the genetic determinants of the donor plant and the tester plant have been proven to be equivalent or the same.

In a further embodiment, the invention relates to a spinach plant which may comprise the genetic determinant of the invention, wherein said genetic determinant is obtainable by introgression from a plant grown from seed that was deposited with the NCIMB under accession numbers NCIMB 41954, NCIMB 41955 or NCIMB 41956.

The invention further provides a spinach plant which may comprise a genetic determinant that leads to the plant having a red colouration of the leaves, wherein at least part of the cells of the epidermis of the spinach leaf between the veins of at least the adaxial leaf surface, preferably both the adaxial and abaxial leaf surface, comprise a red pigment, wherein said genetic determinant is introgressed from a plant grown from seed that was deposited with the NCIMB under accession numbers NCIMB 41954, NCIMB 41955 or NCIMB 41956.

"Introgression" as used in this application is intended to mean introduction of a trait into a plant not carrying the trait by means of crossing and selecting.

According to a further aspect thereof, the invention relates to seeds of the spinach plants, that comprise the genetic determinant that leads to the plant having the red colouration of the leaves of the invention, as found in seeds with deposit accession numbers NCIMB 41954, NCIMB 41955 or NCIMB 41956. A seed of the invention may either comprise the genetic determinant heterozygously or homozygously.

The invention also relates to seed of the spinach (*Spinacia oleracea* L.) plant of the invention that is capable of growing into a spinach plant of the invention.

In addition, the invention relates to use of a plant of the invention, as germplasm in a breeding programme for the development of spinach plants having a red colouration of the leaves, wherein the red colouration of the leaves is the result of at least part of the cells of the epidermis of the spinach leaf between the veins of at least the adaxial leaf surface, preferably both the adaxial and abaxial leaf surface, which may comprise a red pigment.

The invention also relates to progeny of a spinach plant of the invention, which shows the red colouration of the leaves of the invention. Such progeny may be produced by sexual or vegetative reproduction of a plant of the invention or a progeny plant thereof. The progeny carries the genetic determinant that causes the trait of the invention and that is as found in seed with deposit accession numbers NCIMB 41954, NCIMB 41955 and NCIMB 41956, either in homozygous or heterozygous form.

When the genetic determinant of the invention is homozygously present, the progeny plant displays the trait of the invention in the same or in a similar way as the plant grown from seed of which a representative sample was deposited under accession numbers NCIMB 41954, NCIMB 41955 and NCIMB 41956. This means that such progeny has the same red colouration of the leaves as claimed for the spinach plant of the invention. In addition to this, the plant may be modified in one or more other characteristics. Such additional modifications are for example effected by mutagenesis or by transformation with a transgene.

As used herein the word "progeny" is intended to mean the offspring or the first and all further descendants from a cross with a plant of the invention that shows the trait of the invention and/or carries the genetic determinant underlying the trait. Progeny of the invention may comprise descendants of any cross with a plant of the invention that carries the genetic determinant causing the trait of the invention. Such progeny is for example obtainable by crossing a first spinach plant with a second spinach plant, wherein one of the plants was grown from seeds of which a representative sample was deposited under accession numbers NCIMB 41954, NCIMB 41955 and NCIMB 41956, but may also be the progeny of any other spinach plant carrying the genetic determinant as present in NCIMB 41954, NCIMB 41955 and NCIMB 41956.

The said progeny plants comprise a genetic determinant that may comprise one or more Quantitative Trait Loci (QTLs) causing the phenotypic trait of the invention, wherein the said genetic determinant is obtainable from a spinach plant grown from seeds of which a representative sample was deposited under NCIMB accession numbers NCIMB 41954, NCIMB 41955 and NCIMB 41956. The trait of the invention thus has a genetic basis in the genome of a spinach plant, and for example by using the phenotyping method described in Example 1 spinach plants may be identified as being plants of the invention.

The invention further relates to parts of a spinach plant of the invention that are suitable for sexual and vegetative reproduction, i.e. propagation material, wherein said propagation material may comprise the genetic determinant causing trait of the invention. Such parts are for example selected from the group consisting of microspores, pollen, ovaries, ovules, embryo sacs and egg cells.

In addition, the invention relates to parts of the spinach plant of the invention that are suitable for vegetative reproduction, in particular cuttings, roots, stems, cells, protoplasts, callus and tissue cultures of the spinach plant of the invention. The tissue culture may comprise regenerable cells, such a tissue culture may be derived from leaves, pollen, embryos, cotyledons, hypocotyls, meristematic cells, root tips, anthers, flowers, seeds and stems. The propagation material carries the genetic determinant that causes the trait of the invention, either in homozygous or heterozygous form.

The invention further relates to a spinach plant grown or regenerated from the said propagation material of a plant of the invention, which spinach plant has a red colouration of the leaves, wherein the red colouration of the leaves is the result of at least part of the cells of the epidermis of the spinach leaf between the veins of at least the adaxial leaf surface, preferably both the adaxial and abaxial leaf surface, which may comprise a red pigment. The genetic determinant underlying the phenotypic trait of the invention is as present in seeds as deposited under accession numbers NCIMB 41954, NCIMB 41955 and NCIMB 41956.

The invention relates to a cell of a spinach plant of the invention, which cell may comprise a genetic determinant which leads to the plant having a red colouration of the leaves of the invention, wherein the said determinant is present in a spinach plant grown from seeds of which a representative sample was deposited with the NCIMB under accession numbers NCIMB 41954, NCIMB 41955 and NCIMB 41956. Said spinach plant is obtainable by crossing a spinach plant with a second spinach plant, in particular a spinach plant grown from seed as deposited under accession number NCIMB 41954, NCIMB 41955 or NCIMB 41956, and selecting for a spinach plant that has the trait of the invention. The said cell thus may comprise the genetic information encoding said trait of the invention, in particular genetic information which is substantially identical, preferably completely identical to the genetic information encoding the said trait of the spinach plant grown from seeds of which a representative sample was deposited under accession numbers NCIMB 41954, NCIMB 41955 and NCIMB 41956, more in particular the genetic determinant described herein. Preferably, the cell of the invention is part of a plant or plant part, but the cell may also be in isolated form.

In one embodiment, the invention relates to the use of seeds with NCIMB accession number NCIMB 41954, NCIMB 41955 or NCIMB 41956, for transferring the genetic determinant of the invention, which confers the trait of the invention, into another spinach plant.

In another embodiment, the invention relates to the use of a spinach plant, which plant carries the genetic determinant of the invention, which confers the trait of the invention, as present in and obtainable from a spinach plant, grown from seed with NCIMB accession number NCIMB 41954, NCIMB 41955 or NCIMB 41956, as a crop.

The invention also relates to the use of a spinach plant, which carries the genetic determinant of the invention which confers the trait of the invention, as present in a spinach plant, in particular a spinach plant grown from seed with NCIMB accession number NCIMB 41954, NCIMB 41955 or NCIMB 41956, as a source of seed.

In yet another embodiment, the invention relates to the use of a spinach plant, which carries the genetic determinant which confers the trait of the invention as present in a spinach plant, in particular a spinach plant grown from seed with NCIMB accession number NCIMB 41954, NCIMB 41955 or NCIMB 41956, as a source of propagating material.

Further, the invention relates to the use of a spinach plant, which carries the genetic determinant which confers the trait of the invention, as present in a spinach plant, in particular a spinach plant grown from seed with NCIMB accession number NCIMB 41954, NCIMB 41955 or NCIMB 41956, for consumption.

In another embodiment, the invention relates to the use of a spinach plant, which carries the genetic determinant which confers the trait of the invention, alleles as present in seeds with NCIMB accession number NCIMB 41954, NCIMB 41955 or NCIMB 41956, for conferring the genetic determinant that leads to the trait of the invention to a spinach plant.

In yet another embodiment, the invention relates to the use of a spinach plant, as a recipient of the genetic determinant as present in seeds with NCIMB accession number NCIMB 41954, NCIMB 41955 and NCIMB 41956.

In one embodiment, the invention relates to spinach plants that comprise the genetic determinant causing the trait of the invention and that have acquired said genetic determinant by introduction of the genetic information that is responsible for the trait from a suitable source, either by conventional breeding, or genetic modification, in particular by cisgenesis or transgenesis. Cisgenesis is genetic modification of plants with a natural gene, encoding an (agricultural) trait from the crop plant itself or from a sexually compatible donor plant. Transgenesis is genetic modification of a plant with a gene from a non-crossable species or with a synthetic gene.

In one embodiment, the source from which the genetic information is acquired, in particular the genetic determinant, is formed by plants grown from the deposited seeds, or by sexual or vegetative descendants thereof.

The invention also relates to harvested parts of spinach plants of the invention or parts thereof, to food products which may comprise harvested parts, in particular leaves, of *Spinacia oleracea* plants of the invention or parts thereof, either in natural or optionally in processed form.

The harvested part or food product may be or may comprise a stem, a leaf, a petiole, a root, a sprout, an inflorescence, a flower, or any other part of a spinach plant. The food product or harvested part, may have undergone one or more processing steps. Such a processing step might comprise but is not limited to any one of the following treatments or combinations thereof: cutting, washing, cooking, steaming, baking, frying, pasteurizing, freezing, grinding, extracting oil, pickling, or fermenting. The processed form that is obtained is also part of this invention.

In a further embodiment, the invention relates to a container which may comprise one or more spinach plants of the invention in a growth substrate for harvest of leaves from the spinach plant in a domestic environment.

In one aspect the invention relates to a method for production of a spinach plant which leads to the plant having the trait of the invention, which may comprise
   a) crossing a plant which may comprise a genetic determinant that leads to the trait with another plant;
   b) optionally selecting plants in the resulting F1 that have the genetic determinant and selfing the resulting F1 plants that have the genetic determinant for obtaining F2 plants;
   c) selecting plants that have the trait in the F2;
   d) optionally performing one or more additional rounds of selfing or crossing, and subsequently selecting, for a plant which may comprise/showing the trait of the invention.

The word "trait" in the context of this application refers to the phenotype of the plant. In particular, the word "trait" refers to the trait of the invention, more in particular to the trait of having a red colouration of the leaves, wherein the red colouration of the leaves is the result of at least part of the cells of the epidermis of the spinach leaf between the veins of at least the adaxial leaf surface, preferably both the adaxial and abaxial leaf surface, which may comprise a red pigment. The term "genetic determinant" is used for the genetic information in the genome of the plant that causes the trait of the invention. When a plant shows the trait of the invention, its genome may comprise the genetic determinant causing the trait of the invention. The plant thus has the genetic determinant of the invention.

It is clear that the parent that provides the trait of the invention is not necessarily a plant grown directly from the deposited seeds. The parent may also be a progeny plant from the seed or a progeny plant from seeds that are identified to have the trait of the invention by other means.

In one aspect, the invention relates to a method for production of a spinach plant which leads to the plant having the trait of the invention, which may comprise
   e) crossing a plant which may comprise the genetic determinant that leads to the trait with another plant;
   f) optionally backcrossing the resulting F1 with the preferred parent;
   g) selecting for plants that have the trait in the F2;
   h) optionally performing one or more additional rounds of selfing or crossing, and subsequently selecting, for a plant which may comprise the trait.

The invention additionally provides a method of introducing another desired trait into a *Spinacia oleracea* plant which has the trait of the invention, which may comprise:
   i) crossing a spinach plant that has the trait of the invention, representative seed of which were deposited under deposit numbers NCIMB 41954, NCIMB 41955 and NCIMB 41956, with a second spinach plant that may comprise a desired trait to produce F1 progeny;
   j) selecting an F1 progeny that may comprise said trait of the invention and the desired trait;
   k) crossing the selected F1 progeny with either parent, to produce backcross progeny;

l) selecting backcross progeny which may comprise the desired trait and the trait of the invention; and m) optionally repeating steps c) and d) one or more times in succession to produce selected fourth or higher backcross progeny that may comprise the desired trait and the trait of the invention. The invention includes a spinach plant produced by this method.

In one embodiment selection for plants having the trait of the invention is done in the F1 or any further generation. In another aspect selection for the trait of the invention is started in the F2 of a cross or alternatively of a backcross. Selection of plants may be done phenotypically which indirectly detects the genetic determinant underlying the trait.

In one embodiment selection for plants having the trait of the invention is started in the F3 or a later generation.

In one embodiment the plant which may comprise the genetic determinant is a plant of an inbred line, a hybrid, a doubled haploid, or of a segregating population.

The invention further provides a method for the production of a spinach plant having the trait of the invention by using a doubled haploid generation technique to generate a doubled haploid line which may comprise the said trait.

The invention furthermore relates to hybrid seed that may be grown into a plant having the trait of the invention and to a method for producing such hybrid seed comprising crossing a first parent plant with a second parent plant and harvesting the resultant hybrid seed, wherein said first parent plant and/or said second parent plant is the plant as claimed.

In one embodiment, the invention relates to a method for producing a hybrid spinach plant that has the trait of the invention, which may comprise crossing a first parent spinach plant with a second parent spinach plant and harvesting the resultant hybrid seed, of which the first parent plant and/or the second parent plant has the trait of the invention, and growing said hybrid seeds into hybrid plants having the trait of the invention.

The invention also relates to a method for the production of a spinach plant having the trait of the invention by using a seed that may comprise a genetic determinant in its genome that leads to the trait of the invention, for growing the said spinach plant. The seeds are suitably seeds of which a representative sample was deposited with the NCIMB under deposit numbers NCIMB 41954, NCIMB 41955 and NCIMB 41956.

The invention also relates to a method for seed production which may comprise growing spinach plants from seeds of which a representative sample was deposited with the NCIMB under deposit numbers NCIMB 41954, NCIMB 41955 and NCIMB 41956, allowing the plants to produce seeds, and harvesting those seeds. Production of the seeds is suitably done by crossing or selfing.

In one embodiment, the invention relates to a method for the production of a spinach plant having the trait of the invention by using tissue culture.

The invention furthermore relates to a method for the production of a spinach plant having the trait of the invention by using vegetative reproduction.

In one embodiment, the invention relates to a method for the production of a spinach plant having the trait of the invention by using a method for genetic modification to introgress the said trait into the spinach plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of spinach plants that have the trait of the invention wherein germplasm which may comprise said trait is used. Representative seed of said plant comprising the genetic determinant and being representative for the germplasm was deposited with the NCIMB under deposit numbers NCIMB 41954, NCIMB 41955 and NCIMB 41956.

In a further embodiment the invention relates to a method for the production of a spinach plant having the trait of the invention wherein progeny or propagation material of a plant which may comprise the genetic determinant conferring said trait is used as a source to introgress the said trait into another spinach plant. Representative seed of said plant which may comprise the genetic determinant was deposited with the NCIMB under deposit numbers NCIMB 41954, NCIMB 41955 and NCIMB 41956.

The invention provides preferably a spinach plant having the trait of the invention, which plant is obtainable by any of the methods herein described and/or familiar to the skilled person.

The term "trait of the invention" as used herein is defined as the trait which leads to the spinach plant of the invention having a red colouration of the leaves, wherein the red colouration of the leaves is the result of at least part of the cells of the epidermis of the spinach leaf between the veins of at least the adaxial leaf surface, preferably both the adaxial and abaxial leaf surface, which may comprise a red pigment.

Although the present invention and its advantages have been described in detail, it should be understood that various changes, substitutions and alterations may be made herein without departing from the spirit and scope of the invention as defined in the appended claims.

The invention will be further illustrated in the examples that follow and that are only given for illustrative purposes and in no way intended to be limiting on the scope of the invention.

EXAMPLES

Example 1

Phenotypic Characterization of Plants of the Invention

Plants of the invention carrying the genetic determinant homozygously could be identified easily when grown under normal growing conditions in the greenhouse or on the field from the moment the first two leaves of the plants are fully grown, by their red petioles and the red colouration of their leaves (see FIG. 2A). Red colouration was scored using the RHS colour chart (The Royal Horticultural Society, London, UK). Both the upper (adaxial) and lower (abaxial) surface of the leaf blades of plants of the invention carrying the genetic determinant homozygously had a purple-red colour (see FIG. 3A+B) that was scored as 187A, N186C or in some cases N186B, all in the greyed-purple group.

The colour of the petiole and the colour of the epidermal layer at the primary vein, also called midvein or midrib, was usually lighter than that of the rest of the leaf blade. On the abaxial surface of the leaves the secondary veins were usually also marked by a lighter colour than the rest of the leaf blade. The colour of the petioles of leaves of plants of the invention carrying the genetic determinant homozygously was scored 187B, 187C, 187D or N186D, all in the greyed-purple group. At the primary vein of the leaf blade the colour was scored 187A, 187B, 187C, 187D, N186C or N186D, while the colour at the secondary veins on the abaxial surface of the leaves was scored 187A, 187B, 187C or 187D, all in the greyed-purple group.

Plants carrying the genetic determinant of the invention heterozygously had red petioles and green leaf blades with red primary and secondary veins and additional reddish colouration in the leaf areas of the adaxial surface of the leaf in between these veins (see FIG. 2B).

The percentage of the leaf showing a reddish colouration in plants carrying the genetic determinant of the invention heterozygously differs from one genetic background to another, but is always higher than in red vein spinach plants not carrying the genetic determinant of the invention, when grown under identical or similar circumstances.

In some plants carrying the genetic determinant of the invention heterozygously the red colouration may be more confined to the areas close to the major veins of the leaf, whereas in other plants carrying the genetic determinant of the invention heterozygously the red pigment may be present in leaf epidermal cells almost throughout the leaf blade.

When a transverse section was made of the leaf of a plant of the invention carrying the genetic determinant homozygously it became clear the red pigment causing the red colouration of the leaves was primarily localised in the epidermal layer of the leaf (see FIG. 3H), both on the adaxial and abaxial side of the leaf (see FIG. 3G). The mesophyll containing the chlorophyll (with a green colour) below the outermost 1 to 3 cell layers is unaffected (see FIG. 3H), as compared to a plant not containing the genetic determinant of the invention.

When a transverse section of a leaf is made using fresh leaf tissue (i.e. not fixed or embedded) the red pigment may leak out of damaged cells and also make cells that did not contain the red pigment themselves seem red.

Additionally, plants of the invention were analysed by examining whether the cells of the epidermis of the spinach leaf between the veins of at least the adaxial leaf surface, preferably both the adaxial and abaxial leaf surface, are red.

Epidermal strips, of e.g. 0.15×0.2 cm, were taken from between the veins of the adaxial and abaxial leaf surface. The epidermis was first cut along 3 sides of the strip to be taken. One fine point of the forceps was inserted between the epidermis and the mesophyll along the remaining side. Then the epidermis was grasped and slowly stripped from the mesophyll. Strips were then transferred to a microscope slide with a drop of water on it, and were covered with a cover slip. After this the colour of the cells of the epidermal strips was examined under a transmission light microscope.

In order to avoid confusion it is important to take such epidermal strips for analysis from a leaf blade area well removed from red coloured veins.

When taking and examining these epidermal strips great care must be taken not to damage and pierce any epidermal cells, as this causes the red pigment to leak out of the cells and the percentage of cells containing red pigment in the epidermis to be underestimated.

In plants of the invention carrying the genetic determinant homozygously about 90-100% of the epidermal cells, excluding the guard cells that make up the stomata, in the epidermal strip had a bright red-pink colour and thus comprise the red pigment (see FIG. 3C). In plants carrying the genetic determinant of the invention heterozygously 18-67% of the epidermal cells in the epidermal strip had a red/pink colour (see FIG. 3D), the percentage depending on how close to the veins the epidermis strip was taken.

None of the cells of epidermal strips taken from between the veins of the adaxial or abaxial leaf surface of both spinach plants with green leaves (see FIG. 3E) and spinach plants with green leaves with red petioles and red major veins, wherein the red colouration was confined to the petioles and the epidermis above the major veins (red veined spinach)(see FIG. 3F) had a red-pink colour. None of these cells therefore showed a detectable level of betacyanins, as far as quantifiable using this method.

Example 2

Biochemical Analysis of Plants of the Invention

Plants of the invention were analysed for chlorophyll and betacyanin content, and compared with green spinach plants and spinach plants with green leaves with red petioles and red major veins, wherein the red colouration was confined to the petioles and the epidermis above the major veins (red veined spinach, as shown in FIG. 2D). All plants were grown in soil in an unheated greenhouse in Fijnaart, the Netherlands, in the winter of 2011-2012. Both the chlorophyll and betacyanin levels were measured using a biochemical method.

Total chlorophylls (chlorophyll a and b) were measured at absorbances of 653 nm and 667 nm, while betacyanin was measured at an absorbance of 537 nm. For each spinach variety, a representative sample of about 200 grams of fresh weight of the above ground portion of the spinach plant was harvested at the mature leaf stage. For each spinach line two samples of 5-10 plants each were taken to serve as replicates.

Samples were placed in plastic bags and immediately frozen at <−80° C. Frozen samples were pulverized by hand. The pulverized leaf material was then ground in a Grindomix (Retsch, 5" 3000 rpm followed by 5" 5000 rpm) using the free floating lid in presence of as little liquid nitrogen as necessary (sample should be kept frozen) to obtain a powder. This powder was then transferred to a tube that was chilled with liquid nitrogen and was stored at <−70° C. until further analysis.

For chlorophyll measurements one gram of the powder (the exact mass was noted) was transferred into each of two 60 ml flasks. 50 ml 100% methanol was immediately added to the two flasks. The volume (ml) used was noted. The sample solution was homogenated with an Ultra Turrax for 1 minute and sonicated in an ultrasonic bath for 5 minutes at 'set degas'. A part of the solution was put in a 1.5 ml eppendorf tube and centrifuged at 4° C. at 13,000 rpm for 4 min. The spectrum of 360-900 nm was measured and the absorbances at 653 nm and 667 nm were determined (if necessary after dilution with extraction liquid). The amount of total chlorophyll was calculated using the following formula:

$$\text{Total chlorophyll} = 25.5 * A_{653} + 4 * A_{667} \text{ (µg/ml methanol extract)}$$

with a correction for the dilution and conversion to µg/g sample fresh weight. The formula used to calculate the level of total chlorophyll was taken from Goodwin T. W. (1976; Chemistry and Biochemistry of Plant Pigments, Volume 2, Chapter 18, incorporated herein by reference).

For betacyanin measurements 10 grams of the powder (exact mass was noted) was transferred into each of two 50 ml tubes. An amount of 4 to 5 times the sample volume of Potassium phosphate buffer (250 mM, pH=5) was added to the two tubes. The mass (g) of the buffer used was noted. The sample solution was sonicated in an ultrasonic bath for 5 minutes at 'set degas'. A part of the solution was put in a 12 ml tube for possible reanalyses. A part of the solution was transferred to a 1.5 ml eppendorf tube and centrifuged at 4° C. at 13,000 rpm for 4 min. The spectrum of 400-800 nm was measured and the absorbance at 537 nm was determined (if necessary after dilution with extraction liquid).

The amount of betacyanin was calculated with a formula which uses the extinction coefficient of betanin in the Potassium phosphate buffer (250 mM, pH=5) used. Betacyanin content is thus given in µg betanin equivalents/g fresh weight (FW).

Betanin equivalents (µg/g fresh weight)=
(10*$A_{537}$*dilution*(mass buffer+mass liquid
part sample))/(1.1599*mass sample)

wherein 1.1599 is the $A_{537}$ of a solution 1 mg/100 ml betanin in the Potassium phosphate buffer (250 mM, pH=5) used, and the mass of the liquid part of the sample is calculated by multiplying the mass of the sample (=10 g) by (1−(percentage dry matter/100)).

TABLE 1

|  | Squirrel | RZ red vein spinach line | 12.30002 | 12.30007 | 12.30009 |
|---|---|---|---|---|---|
| Betanin equivalents |  |  |  |  |  |
| Sample 1 (µg/g FW) | 5 | 40 | 450 | 340 | 420 |
| Sample 2 (µg/g FW) | 3 | 50 | 450 | 340 | 450 |
| Mean (µg/g FW) | 4 | 43 | 450 | 340 | 440 |
| Total Chlorophyll |  |  |  |  |  |
| Sample 1 (µg/g FW) | 1355 | 1344 | 1311 | 1178 | 1393 |
| Sample 2 (µg/g FW) | 1214 | 1452 | 1408 | 1085 | 1316 |
| Mean (µg/g FW) | 1285 | 1398 | 1359 | 1132 | 1354 |
| Total Chlorophyll/ Betanin equivalents |  |  |  |  |  |
| Sample 1 (µg/g FW) | 271.0 | 33.6 | 2.9 | 3.5 | 3.3 |
| Sample 2 (µg/g FW) | 404.7 | 29.0 | 3.1 | 3.2 | 2.9 |
| Mean | 337.8 | 31.3 | 3.0 | 3.3 | 3.1 |

Chlorophyll and betacyanin measurements of plants of the invention, green spinach plants and spinach plants with green leaves with red petioles and red major veins, wherein the red colouration was confined to the petioles and the epidermis above the major veins. All plants were grown in soil in an unheated greenhouse in Fijnaart, the Netherlands, in the winter of 2011-2012. Squirrel is a green Rijk Zwaan spinach variety. Rijk Zwaan red vein spinach line has plants with green leaves with red petioles and red major veins, wherein the red colouration is confined to the petioles and the epidermis at the major veins. Populations of plants of the invention of line 12.30002, 12.30007 and 12.30009 were grown from seeds of the deposits and contained only plants that carried the genetic determinant homozygously. The mean values given for betacyanin and chlorophyll content are the mean of two biological replicates per plant line of 5-10 plants each.

As is clear from Table 1 the betacyanin levels (betanin equivalents per gram fresh weight) of plants of the invention carrying the genetic determinant homozygously were significantly higher than those measured for WT spinach with green leaves with green petioles (about 100 times higher) and those measured for WT spinach plants with green leaves with red petioles and red major veins, wherein the red colouration is confined to the petioles and the epidermis above the major veins (about 10 times higher).

Interestingly, the chlorophyll levels were not changed in plants of the invention carrying the genetic determinant homozygously, as compared to WT green spinach and WT red vein spinach (see Table 1).

As the chlorophyll levels were quite similar for all different lines (Squirrel, RZ red vein spinach line and the three lines of plants of the invention carrying the genetic determinant homozygously) while the betacyanin levels did differ considerably, the ratio between total chlorophyll (µg/g fresh weight) and betacyanin (µg betanin equivalents/g fresh weight) also differed clearly between plants of the invention carrying the genetic determinant homozygously and both WT spinach lines (see Table 1).

Example 3

Transfer of the Trait of the Invention to Other Spinach Plants

Spinach plants which may comprise the genetic determinant, that leads to the plant having a red colouration of the leaves, in a homozygous state, as found in representative seed as deposited under deposit accession numbers NCIMB 41954, NCIMB 41955 and NCIMB 41956 (called herein the donor), were crossed with several different wild type (WT) spinach plants not carrying the trait of the invention.

In spinach crosses it is not uncommon for some self pollination to occur. To enable easy detection of occasional occurrences of self pollination, the donor parent was used as the pollinator or father in these crosses. If certain supposed F1 plants grown from the seeds harvested from the WT mother plant had a phenotype very similar to that of the WT mother, and the F2 plants obtained by self pollination of those supposed F1 plants also looked like the original WT mother plant, it was concluded those plants resulted from a self pollination of the WT mother plant and they were discarded.

Unexpectedly, the resulting F1 plants from this cross had a leaf colouration phenotype that was intermediate between the phenotype of the WT parent and that of spinach plants which may comprise the genetic determinant that leads to the plant having a red colouration of the leaves homozygously (donor parent). This suggests a semi-dominant inheritance of the trait of the invention. These F1 plants had red petioles and leaf blades with red primary and secondary veins and additional reddish colouration on the adaxial leaf surface in the leaf areas in between these veins (see FIG. 2B). This was the case both for F1 plants resulting from a cross in which the WT parent had green leaves and petioles, and for F1 plants resulting from a cross in which the WT parent had green leaves with red petioles and red major veins, wherein the red colouration is confined to the petioles and the epidermis above the major veins.

The WT spinach plant into which the trait of the invention may be introduced may be a spinach plant of any leaf type, any form or any colouring.

Subsequently, these F1 plants were self pollinated and F2 plants were obtained. The different F2's segregated in a manner that corresponds with a monogenic semi-dominant, also called incomplete dominant, inheritance of the trait of the invention. The result in the F2 was approximately one plant with the WT parent leaf colouration to one plant with the red leaf colouration of the donor parent to two plants with an intermediate phenotype with green leaves with red petioles and leaf blades with red primary and secondary veins and additional reddish colouration on the adaxial leaf surface in the leaf areas in between these veins (see Table 2 and FIG. 2).

TABLE 2

| cross | | reddish | red | total | Chi-square probability | p > 0.05? |
|---|---|---|---|---|---|---|
| | green | | | | | |
| 1 | observed | 8 | 14 | 8 | 30 | 0.936 | yes |
| | expected | 7.5 | 15 | 7.5 | 30 | | |
| 2 | observed | 48 | 125 | 43 | 216 | 0.061 | yes |
| | expected | 54 | 108 | 54 | 216 | | |
| 3 | observed | 57 | 101 | 52 | 210 | 0.762 | yes |
| | expected | 52.5 | 105 | 52.5 | 210 | | |
| | red vein | | | | | |
| 4 | observed | 7 | 15 | 8 | 30 | 0.967 | yes |
| | expected | 7.5 | 15 | 7.5 | 30 | | |
| 5 | observed | 48 | 91 | 38 | 177 | 0.530 | yes |
| | expected | 44.3 | 88.5 | 44.3 | 177 | | |
| 6 | observed | 35 | 86 | 34 | 155 | 0.391 | yes |
| | expected | 38.8 | 77.5 | 38.8 | 155 | | |

Segregations of the trait of the invention in 3 F2 populations from crosses of the donor parent (father) with a different WT green spinach parents (green), and 3 F2 populations from crosses of the donor parent (father) with different parent spinach plants with green leaves with red petioles and red major veins, wherein the red colouration is confined to the petioles and the epidermis above the major veins (red vein).

Chi-square tests confirm that the observed numbers of F2 plants that had the WT parental phenotype (either green or red vein), the donor parent phenotype (red) and the intermediate phenotype (reddish) were in agreement with what is expected if a trait segregates in a semi-dominant fashion, namely 1:1:2 (WT parent phenotype: donor parent phenotype: intermediate phenotype). The chi-square probability values are above 0.05 in all these populations. From the segregation data in Table 2 it may thus be concluded that the genetic determinant of the invention behaves as a monogenic semi-dominant trait.

The invention is further described by the following numbered paragraphs.

1. Spinach plant (*Spinacia oleracea*) comprising a genetic determinant that leads to the plant having a red colouration of the leaves, wherein at least part of the cells of the epidermis of the spinach leaf between the veins of at least the adaxial leaf surface, preferably both the adaxial and abaxial leaf surface, comprise a red pigment, which genetic determinant is as comprised in a spinach plant representative seed of which was deposited with the NCIMB under accession numbers NCIMB 41954, NCIMB 41955 and NCIMB 41956.

2. Spinach plant according to paragraph 1, wherein the genetic determinant is homozygously present.

3. Spinach plant according to paragraph 1, wherein the betacyanin content of the leaves at harvest stage is at least, in order of increased preference, 90 µg betanin equivalents/g fresh weight, 100 µg betanin equivalents/g fresh weight, 110 µg betanin equivalents/g fresh weight, 120 µg betanin equivalents/g fresh weight, 130 µg betanin equivalents/g fresh weight, 140 µg betanin equivalents/g fresh weight, 150 µg betanin equivalents/g fresh weight, 160 µg betanin equivalents/g fresh weight, 170 µg betanin equivalents/g fresh weight, 180 µg betanin equivalents/g fresh weight, 190 µg betanin equivalents/g fresh weight, 200 µg betanin equivalents/g fresh weight, 210 µg betanin equivalents/g fresh weight, 220 µg betanin equivalents/g fresh weight, 230 µg betanin equivalents/g fresh weight, 240 µg betanin equivalents/g fresh weight, 250 µg betanin equivalents/g fresh weight, 300 µg betanin equivalents/g fresh weight, 350 µg betanin equivalents/g fresh weight, 400 µg betanin equivalents/g fresh weight, 450 µg betanin equivalents/g fresh weight, 500 µg betanin equivalents/g fresh weight, 550 µg betanin equivalents/g fresh weight, 600 µg betanin equivalents/g fresh weight.

4. Spinach plant according to any one of the paragraphs 1-3, obtainable by crossing a first spinach plant with a second spinach plant, wherein at least one of the said plants comprises the genetic determinant as comprised in a spinach plant representative seed of which was deposited with the NCIMB under accession numbers NCIMB 41954, NCIMB 41955 and NCIMB 41956, or a progeny plant thereof carrying the genetic determinant, and selecting, preferably in the F2 generation, for plants having a red colouration of the leaves, wherein at least part of the cells of the epidermis of the spinach leaf between the veins of at least the adaxial leaf surface, preferably both the adaxial and abaxial leaf surface, comprise a red pigment.

5. Seed of a spinach plant according to any one of the paragraphs 1-4, wherein the seed comprises the genetic determinant as present in seeds of which a representative sample was deposited with the NCIMB under accession numbers NCIMB 41954, NCIMB 41955 and NCIMB 41956.

6. Progeny plant of a spinach plant according to any one of the paragraphs 1-4 or of spinach seed according to paragraph 5, wherein the plant comprises the genetic determinant as present in seeds of which a representative sample was deposited with the NCIMB under accession numbers NCIMB 41954, NCIMB 41955 and NCIMB 41956.

7. Progeny plant according to paragraph 6, wherein the genetic determinant is homozygously present.

8. Propagation material derived from a plant according to any one of the paragraphs 1-4 and 6-7 or seed according to paragraph 5, wherein the propagation material comprises the genetic determinant as present in seeds of which a representative sample was deposited with the NCIMB under accession numbers NCIMB 41954, NCIMB 41955 and NCIMB 41956.

9. Propagation material capable of growing into a plant according to any one of the paragraphs 1-4.

10. Propagation material according to paragraph 8 or 9, wherein the propagation material is selected from a group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, callus, and cells.

11. Tissue culture of propagation material according to any one of the paragraphs 8-10.

12. A spinach leaf of a plant according to any one of the paragraphs 1-4 and 6-7 having a red colouration, wherein at least part of the cells of the epidermis of the spinach leaf between the veins of at least the adaxial leaf surface, preferably both the adaxial and abaxial leaf surface, comprise a red pigment.

13. Food product, comprising spinach leaves of claim 12, or parts thereof, optionally in processed form.

14. Use of a plant according to any one of the paragraphs 1-4 and 6-7, or plants produced from the seed of claim 5 or from the propagation materials according to any one of the paragraphs 8-10, as germplasm in a breeding programme for the development of spinach plants having a red colouration of the leaves, wherein the red colouration of the leaves is the result of at least part of the cells of the epidermis of the spinach leaf between the veins of at least the adaxial leaf surface, preferably both the adaxial and abaxial leaf surface, comprising a red pigment.

15. Container comprising one or more spinach plants according to any of the paragraphs 1-4, and 7-8 in a growth substrate for harvest of leaves from the spinach plant in a domestic environment.

Having thus described in detail preferred embodiments of the present invention, it is to be understood that the invention defined by the above paragraphs is not to be limited to particular details set forth in the above description as many apparent 25 variations thereof are possible without departing from the spirit or scope of the present invention.

The invention claimed is:

1. A *Spinacia oleracea* plant comprising a genetic determinant that leads to the plant having a red coloration of the leaves, wherein at least part of the cells of the epidermis of the spinach leaf between the veins of at least the adaxial leaf surface, preferably both the adaxial and abaxial leaf surface, comprise a red pigment, which genetic determinant is as comprised in a spinach plant representative seed of which was deposited with the NCIMB under accession numbers NCIMB 41954, NCIMB 41955 and NCIMB 41956.

2. The *Spinacia oleracea* plant as claimed in claim 1, wherein the genetic determinant is homozygously present.

3. The *Spinacia oleracea* plant as claimed in claim 1, wherein the betacyanin content of the leaves at harvest stage is at least, in order of increased preference, 90 µg betanin equivalents/g fresh weight, 100 µg betanin equivalents/g fresh weight, 110 µg betanin equivalents/g fresh weight, 120 µg betanin equivalents/g fresh weight, 130 µg betanin equivalents/g fresh weight, 140 µg betanin equivalents/g fresh weight, 150 µg betanin equivalents/g fresh weight, 160 µg betanin equivalents/g fresh weight, 170 µg betanin equivalents/g fresh weight, 180 µg betanin equivalents/g fresh weight, 190 µg betanin equivalents/g fresh weight, 200 µg betanin equivalents/g fresh weight, 210 µg betanin equivalents/g fresh weight, 220 µg betanin equivalents/g fresh weight, 230 µg betanin equivalents/g fresh weight, 240 µg betanin equivalents/g fresh weight, 250 µg betanin equivalents/g fresh weight, 300 µg betanin equivalents/g fresh weight, 350 µg betanin equivalents/g fresh weight, 400 µg betanin equivalents/g fresh weight, 450 µg betanin equivalents/g fresh weight, 500 µg betanin equivalents/g fresh weight, 550 µg betanin equivalents/g fresh weight, and 600 µg betanin equivalents/g fresh weight.

4. The *Spinacia oleracea* plant as claimed in claim 1, obtainable by crossing a first spinach plant with a second spinach plant, wherein at least one of the said plants comprises the genetic determinant as comprised in a spinach plant representative seed of which was deposited with the NCIMB under accession numbers NCIMB 41954, NCIMB 41955 and NCIMB 41956, or a progeny plant thereof carrying the genetic determinant, and selecting, preferably in the F2 generation, for plants having a red coloration of the leaves, wherein at least part of the cells of the epidermis of the spinach leaf between the veins of at least the adaxial leaf surface, preferably both the adaxial and abaxial leaf surface, comprise a red pigment.

5. A seed of the *Spinacia oleracea* plant as claimed in claim 1, wherein the seed comprises the genetic determinant as present in seeds of which a representative sample was deposited with the NCIMB under accession numbers NCIMB 41954, NCIMB 41955 and NCIMB 41956.

6. A progeny plant of the *Spinacia oleracea* plant as claimed in claim 1 or of the seed as claimed in claim 5, wherein the plant comprises the genetic determinant as present in seeds of which a representative sample was deposited with the NCIMB under accession numbers NCIMB 41954, NCIMB 41955 and NCIMB 41956.

7. The progeny plant as claimed in claim 6, wherein the genetic determinant is homozygously present.

8. A propagation material derived from the plant as claimed in claim 1, wherein the propagation material comprises the genetic determinant as present in seeds of which a representative sample was deposited with the NCIMB under accession numbers NCIMB 41954, NCIMB 41955 and NCIMB 41956.

9. A propagation material derived from the seed as claimed in claim 5, wherein the propagation material comprises the genetic determinant as present in seeds of which a representative sample was deposited with the NCIMB under accession numbers NCIMB 41954, NCIMB 41955 and NCIMB 41956.

10. A propagation material derived from the plant as claimed in claim 6, wherein the propagation material comprises the genetic determinant as present in seeds of which a representative sample was deposited with the NCIMB under accession numbers NCIMB 41954, NCIMB 41955 and NCIMB 41956.

11. A propagation material capable of growing into a plant as claimed in claim 1.

12. The propagation material as claimed in claim 8, wherein the propagation material comprises a microspore, pollen, ovary, ovule, embryo, embryo sac, egg cell, cutting, root, root tip, hypocotyl, cotyledon, stem, leaf, flower, anther, seed, meristematic cell, protoplast, callus, or cell.

13. The propagation material as claimed in claim 9, wherein the propagation material comprises a microspore, pollen, ovary, ovule, embryo, embryo sac, egg cell, cutting, root, root tip, hypocotyl, cotyledon, stem, leaf, flower, anther, seed, meristematic cell, protoplast, callus, or cell.

14. The propagation material as claimed in claim 10, wherein the propagation material comprises a microspore, pollen, ovary, ovule, embryo, embryo sac, egg cell, cutting, root, root tip, hypocotyl, cotyledon, stem, leaf, flower, anther, seed, meristematic cell, protoplast, callus, or cell.

15. The propagation material as claimed in claim 11, wherein the propagation material comprises a microspore, pollen, ovary, ovule, embryo, embryo sac, egg cell, cutting, root, root tip, hypocotyl, cotyledon, stem, leaf, flower, anther, seed, meristematic cell, protoplast, callus, or cell.

16. A tissue culture of propagation material as claimed in claim 8.

17. A tissue culture of propagation material as claimed in claim 9.

18. A tissue culture of propagation material as claimed in claim 10.

19. A tissue culture of propagation material as claimed in claim 11.

20. A spinach leaf of the plant as claimed in claim 1 having a red coloration, wherein at least part of the cells of the epidermis of the spinach leaf between the veins of at least the adaxial leaf surface, preferably both the adaxial and abaxial leaf surface, comprise a red pigment.

21. A spinach leaf of the plant as claimed in claim 6 having a red coloration, wherein at least part of the cells of the epidermis of the spinach leaf between the veins of at least the adaxial leaf surface, preferably both the adaxial and abaxial leaf surface, comprise a red pigment.

22. A food product, comprising the spinach if of claim 20, or parts thereof, optionally in processed form.

23. A food product, comprising the spinach leaf of claim 21, or parts thereof, optionally in processed form.

24. A method of developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface, comprising a red pigment comprising breeding germplasm obtained from a plant of claim 1 with another spinach plant, thereby developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface.

25. A method of developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface, comprising a red pigment, comprising breeding germplasm obtained from a plant of claim 6 with another spinach plant, thereby developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface.

26. A method of developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface, comprising a red pigment, comprising breeding germplasm obtained from a plant of produced from the seed of claim 5 with another spinach plant, thereby developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface.

27. A method of developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface, comprising a red pigment, comprising breeding germplasm obtained from plant obtained from the propagation material of claim 8 with another spinach plant, thereby developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface.

28. A method of developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface, comprising a red pigment, comprising breeding germplasm obtained from plant obtained from the propagation material of claim 9 with another spinach plant, thereby developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface.

29. A method of developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface, comprising a red pigment, comprising breeding germplasm obtained from plant obtained from the propagation material of claim 10 with another spinach plant, thereby developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface.

30. A method of developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface, comprising a red pigment, comprising breeding germplasm obtained from plant obtained from the propagation material of claim 11 with another spinach plant, thereby developing a spinach plant having a red coloration of the leaves, wherein the red coloration of the leaves is the result of at least part of the cells of the epidermis of the spinach leaf between the veins of at least the adaxial leaf surface, preferably both the adaxial and abaxial leaf surface.

31. A container comprising one or more spinach plants as claimed in claim 1 in a growth substrate for harvest of leaves from the spinach plant in a domestic environment.

32. A container comprising one or more spinach plants as claimed in claim 7 in a growth substrate for harvest of leaves from the spinach plant in a domestic environment.

33. A container comprising one or more spinach plants grown from the propagation material as claimed in claim 8 in a growth substrate for harvest of leaves from the spinach plant in a domestic environment.

34. A container comprising one or more spinach plants grown from the propagation material as claimed in claim 9 in a growth substrate for harvest of leaves from the spinach plant in a domestic environment.

35. A container comprising one or more spinach plants grown from the propagation material as claimed in claim 10 in a growth substrate for harvest of leaves from the spinach plant in a domestic environment.

* * * * *

UNITED STATES PATENT AND TRADEMARK OFFICE
CERTIFICATE OF CORRECTION

PATENT NO.       : 9,549,526 B2                                              Page 1 of 1
APPLICATION NO.  : 13/798335
DATED            : January 24, 2017
INVENTOR(S)      : Jan Hugo Den Braber It is certified that error appears in the above-identified patent and that said Letters Patent is hereby corrected as shown below:

In the Claims

Column 25, Line 1 (Claim 22):
Change: "A food product, comprising the spinach if of claim 20"
To: --A food product, comprising the spinach leaf of claim 20--

Signed and Sealed this
Seventh Day of March, 2017

Michelle K. Lee
*Director of the United States Patent and Trademark Office*